United States Patent [19]

Disteldorf et al.

[11] Patent Number: 4,550,208
[45] Date of Patent: Oct. 29, 1985

[54] PREPARATION OF 4,4'-DIAMINOBENZOPHENONES

[75] Inventors: Walter Disteldorf, Wachenheim; Wolfgang Eisfeld, Ludwigshafen; Rolf-Dieter Kohler, Edingen-Neckarhausen, all of Fed. Rep. of Germany

[73] Assignee: BASF Aktiengesellschaft, Ludwigshafen, Fed. Rep. of Germany

[21] Appl. No.: 673,938

[22] Filed: Nov. 21, 1984

[30] Foreign Application Priority Data

Nov. 24, 1983 [DE] Fed. Rep. of Germany ....... 3342462

[51] Int. Cl.$^4$ ............................................. C07C 97/10
[52] U.S. Cl. .................................. 564/329; 564/328; 548/462
[58] Field of Search ............... 564/413, 428, 328, 329; 548/462

[56] References Cited

FOREIGN PATENT DOCUMENTS 484222 10/1974 Australia .
289108 11/1898 Fed. Rep. of Germany .
1102176 3/1961 Fed. Rep. of Germany .
3319650 12/1984 Fed. Rep. of Germany .

OTHER PUBLICATIONS

Fieser & Fieser, *Reagents for Organic Synthesis*, 1975, vol. 5, p. 474, John Wiley & Sons, NY.
Bouanane, et al., Chemical Abstracts, vol. 81, No. 19, 120139w, 1974.
Derwent Abstract, C84–128457, 1984, (DE 319650).

*Primary Examiner*—Charles F. Warren
*Assistant Examiner*—Elizabeth A. Flaherty
*Attorney, Agent, or Firm*—Oblon, Fisher, Spivak, McClelland & Maier

[57] ABSTRACT

4,4'-diaminobenzophenones of the formula I

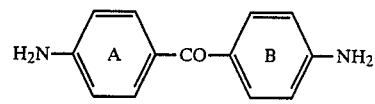

where the rings A and B can be further substituted, are prepared by a process in which a compound of the formula II

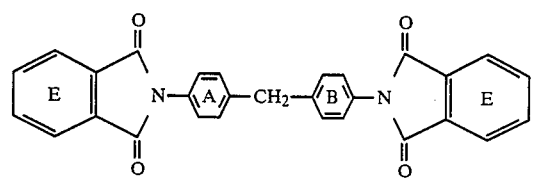

where the rings A, B and E can be substituted, is oxidized with aqueous nitric acid in the presence of nitrobenzene or of an alkanoic acid and under superatmospheric pressure, and the reaction product is cleaved.

The process according to the invention gives the compounds of the formula I in high yield and purity.

5 Claims, No Drawings

PREPARATION OF 4,4'-DIAMINOBENZOPHENONES

The present invention relates to a process for the preparation of 4,4'-diaminobenzophenones of the formula I

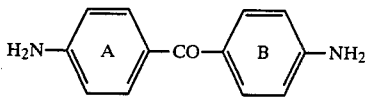

where the rings A and B can be further substituted, wherein a compound of the formula II

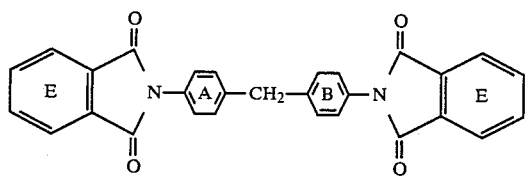

where the rings A, B and E can be further substituted, is oxidized with aqueous nitric acid in the presence of nitrobenzene or of an alkanoic acid and under superatmospheric pressure, and the reaction product is cleaved.

The rings A and B can be substituted by, for example, fluorine, chlorine, bromine or nitro, while examples of substituents for rings E are fluorine, chlorine, bromine, carboxyl and nitro. Alkanoic acids which are particularly suitable for the reaction are those of 2 to 4 carbon atoms, specific examples being mono-, di- and trihaloacetic acids, butyric acid and, preferably, acetic acid and propionic acid.

For the purposes of the present invention, aqueous nitric acid is from 0.5 to 15, preferably from 1 to 4, % strength nitric acid. Advantageously, this nitric acid concentration is established by adding concentrated nitric acid to the reaction mixture consisting of the alkanoic acid, water and the compound of the formula II.

The reaction according to the invention is advantageously carried out at from 100° to 200° C., preferably from 150° to 170° C., in such a way that superatmospheric pressure is established. The upper limit to the pressure is governed by the design of the reaction vessel. The yield has not been found to be pressure-dependent.

Alkanoic acids are used in preference to nitrobenzene, because they give a purer product.

The cleavage of the reaction product can be carried out by a conventional method or by the process described in German Patent Application No. P 3319650.8.

The Examples which follow illustrate the process according to the invention. Parts and percentages are by weight, unless stated otherwise.

The compounds of the formula I are useful intermediates for the preparation of dyes and plastics.

The compounds of the formula II can be prepared by a conventional method, by reacting a compound of the formula

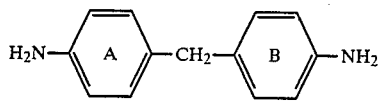

with an anhydride of the formula

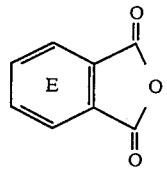

EXAMPLES 1 TO 7

The diphenylmethanes listed in Table 1, together with, in each case, 200 g of alkanoic acid, are heated at 160° C. in a stirred autoclave which is resistant to nitric acid and is equipped with a reflux condenser and a pressure-control valve above the latter, an inert gas being forced in and the pressure-control valve being set at 7 bar. 35.7 g of 53% strength nitric acid are then pumped in over 0.5 hour with temperature and pressure control, with the result that a nitric acid concentration of 3% is established. Oxidation is then continued for a further hour under the same reaction conditions. The final $HNO_3$ concentration is 0.9%. The oxidation mixture is let down to atmospheric pressure and cooled to room temperature, and the precipitated solid is filtered off under suction, washed with water and dried at from 80° to 100° C. under 20 mbar. The corresponding benzophenone is obtained in each case as a 99% pure product. The yields are listed in Table 1.

TABLE 1

| Example No. | Diphenylmethane | Amount (g) | Alkanoic acid | Yield (mol %) |
|---|---|---|---|---|
| 1 | 4,4'-bis-phthalimidoyl-diphenylmethane | 45.8 | Propionic acid | 78.5 |
| 2 | 4,4'-bis(4-carboxyphthalimidoyl)-diphenylmethane | 54.6 | Propionic acid | 91.4 |
| 3 | 4,4'-bis-(4-chlorophthalimidoyl)-diphenylmethane | 52.7 | Propionic acid | 82.6 |
| 4 | 4,4'-bis-(3-chlorophthalimidoyl)-diphenylmethane | 52.7 | Propionic acid | 81.5 |
| 5 | 4,4'-bis-(4,5-dichlorophthalimidoyl)-diphenylmethane | 59.6 | Propionic acid | 86.4 |
| 6 | 4,4'-bis-phthalimidoyl-diphenylmethane | 45.8 | Acetic acid | 71 |
| 7 | 4,4'-bis-phthalimidoyl-2,2'-bis-chlorodiphenylmethane | 52.7 | Propionic acid | 80.3 |

EXAMPLE 8

54.6 g of 4,4'-bis-(4-carboxyphthalimidoyl)-diphenylmethane in 200 g of acetic acid are oxidized at 140° C. and under 5 bar by a procedure similar to that described in Example 1, and the mixture is worked up. 96% pure 4,4'-bis-(4-carboxyphthalimidoyl)-benzophenone is obtained in a yield of 74 mol %.

EXAMPLE 9

45.8 g of 4,4'-bis-phthalimidoyldiphenylmethane in 200 g of nitrobenzene are oxidized at 160° C. and under 7 bar by a procedure similar to that described in Example 1. The nitrobenzene is removed from the oxidation mixture by steam distillation. 85% pure 4,4'-bis-phthalimidoylbenzophenone is obtained in a yield of 73 mol %.

EXAMPLE 10

23 g of 4,4'-bis-phthalimidoylbenzophenone in 46 g of monoethanolamine are stirred for 1 hour at 80° C., after which the mixture is cooled to 20° C. and 200 g of water are then added. The precipitated product is filtered off under suction, washed with water and dried under reduced pressure. 4,4'-Diaminobenzophenone of melting point 241° C. is obtained in a purity >99% and in a yield of 90 mol %.

EXAMPLE 11

27.3 g of 4,4'-bis-(4-carboxyphthalimidoyl)benzophenone are cleaved by a procedure similar to that described in Example 10. 4,4'-Diaminobenzophenone of melting point 241° C. is obtained in a purity >99% and in a yield of 92 mol %.

Using a procedure similar to that described in Example 10, the other compounds of the formula II can also be converted to the amino compounds.

We claim:

1. A process for the preparation of a 4,4'-diaminobenzophenone of the formula I

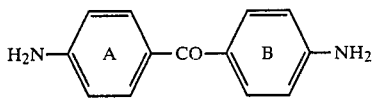

where the rings A and B can be further substituted, wherein a compound of the formula II

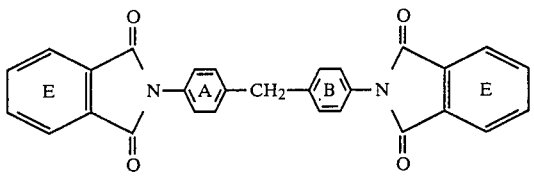

where the rings A, B and E can be substituted, is oxidized with aqueous nitric acid in the presence of nitrobenzene or of an alkanoic acid and under superatmospheric pressure, and the reaction product is cleaved.

2. A process as claimed in claim 1, wherein the oxidation is carried out in the presence of an alkanoic acid.

3. A process as claimed in claim 1, wherein the oxidation is carried out in the presence of acetic acid or propionic acid or a mixture of these acids.

4. A process as claimed in claim 1, wherein the oxidation is carried out using nitric acid having a concentration of from 0.5 to 15%, preferably from 1 to 4%.

5. A process as claimed in claim 1, wherein the oxidation is carried out at from 150° to 170° C.

* * * * *